(12) United States Patent
Sykes et al.

(10) Patent No.: US 11,619,221 B2
(45) Date of Patent: Apr. 4, 2023

(54) PERISTALTIC PUMP

(71) Applicant: Keymed (Medical & Industrial Equipment) Ltd., Southend-on-Sea (GB)

(72) Inventors: Gareth Sykes, Rochford (GB); Mohammed Afzal, Southend-on-Sea (GB)

(73) Assignee: Keymed (Medical & Industrial Equipment) Limited, Southend-on-Sea (GB)

( * ) Notice: Subject to any disclaimer, the term of this patent is extended or adjusted under 35 U.S.C. 154(b) by 600 days.

(21) Appl. No.: 16/603,955

(22) PCT Filed: May 15, 2018

(86) PCT No.: PCT/GB2018/051310
§ 371 (c)(1),
(2) Date: Oct. 9, 2019

(87) PCT Pub. No.: WO2018/211259
PCT Pub. Date: Nov. 22, 2018

(65) Prior Publication Data
US 2020/0124038 A1    Apr. 23, 2020

(30) Foreign Application Priority Data

May 18, 2017 (GB) .................... 1707961

(51) Int. Cl.
*F04B 43/12* (2006.01)
*A61M 3/02* (2006.01)
(Continued)

(52) U.S. Cl.
CPC ........... *F04B 43/1284* (2013.01); *A61M 1/77* (2021.05); *A61M 1/80* (2021.05); *A61M 3/0258* (2013.01);
(Continued)

(58) Field of Classification Search
CPC ...... F04B 43/12; F04B 43/1292; F04B 49/00; F04B 43/082; F04B 43/086;
(Continued)

(56) References Cited

U.S. PATENT DOCUMENTS 3,172,367 A * 3/1965 Kling .................. F04B 43/1215
417/477.13
3,927,955 A * 12/1975 Spinosa ............... F04B 43/1253
417/477.3
(Continued)

FOREIGN PATENT DOCUMENTS

EP    0300625 A1    1/1989
FR    1494561 A     9/1967
(Continued)

OTHER PUBLICATIONS

European Patent Office, International Search Report in International Patent Application No. PCT/GB2018/051310, 5 pp. (dated Jul. 7, 2018).
(Continued)

*Primary Examiner* — Scott J Medway
(74) *Attorney, Agent, or Firm* — Leydig, Voit & Mayer, Ltd.

(57) ABSTRACT

A peristaltic pump comprises a rotor with rollers and first and second tracks mounted on opposites sides of the rotor. Each track is moveable between a first position adjacent the rotor and a second position spaced from the rotor. The tracks may be linked and moveable together so that as one track moves towards the rotor, the other moves away from the rotor and vice versa. In this way, a single pump can be used to provide two different modes of operation, e.g. pumping liquid when one track is adjacent the rotor and applying suction when the other track is adjacent the rotor.

7 Claims, 3 Drawing Sheets

(51) Int. Cl.
*A61M 1/00* (2006.01)
*A61B 1/015* (2006.01)

(52) U.S. Cl.
CPC .......... *F04B 43/1292* (2013.01); *A61B 1/015* (2013.01); *A61M 1/772* (2021.05); *A61M 2205/103* (2013.01)

(58) Field of Classification Search
CPC .. F04B 43/1276; F04B 43/1284; F04B 43/08; F04B 43/1253; A61M 39/10
See application file for complete search history.

(56) References Cited

U.S. PATENT DOCUMENTS

| | | | | |
|---|---|---|---|---|
| 4,025,241 | A * | 5/1977 | Clemens | F04B 43/1284 |
| | | | | 417/477.11 |
| 4,138,205 | A | 2/1979 | Wallach | |
| 4,179,249 | A * | 12/1979 | Guttmann | F04B 43/1284 |
| | | | | 417/477.11 |
| 4,217,993 | A * | 8/1980 | Jess | G05D 7/0676 |
| | | | | 222/14 |
| 4,333,088 | A | 6/1982 | Diggins | |
| 4,365,943 | A * | 12/1982 | Durrum | F04B 43/086 |
| | | | | 417/478 |
| 4,441,867 | A * | 4/1984 | Berelson | F04B 43/1292 |
| | | | | 417/477.1 |
| 5,033,943 | A * | 7/1991 | Durrum | F04B 43/08 |
| | | | | 417/478 |
| 5,082,429 | A * | 1/1992 | Soderquist | F04B 43/1253 |
| | | | | 604/153 |
| 5,158,437 | A * | 10/1992 | Natwick | F04B 43/082 |
| | | | | 417/63 |
| 5,340,290 | A | 8/1994 | Clemens | |
| 5,364,242 | A * | 11/1994 | Olsen | F04B 9/042 |
| | | | | 417/474 |
| 5,447,417 | A * | 9/1995 | Kuhl | F04B 43/1284 |
| | | | | 417/477.11 |
| 5,759,017 | A * | 6/1998 | Patton | F04B 43/1253 |
| | | | | 417/477.7 |
| 6,267,570 | B1 * | 7/2001 | Armando | F04B 43/123 |
| | | | | 417/478 |
| 6,722,865 | B2 * | 4/2004 | Domroese | B25B 5/147 |
| | | | | 417/477.11 |
| 7,287,968 | B2 * | 10/2007 | Haser | F04B 43/1284 |
| | | | | 417/477.9 |
| 7,980,835 | B2 * | 7/2011 | LaBanco | F04B 43/1284 |
| | | | | 417/477.12 |
| 8,453,885 | B2 * | 6/2013 | Breault | F04B 43/12 |
| | | | | 222/383.2 |
| 8,550,310 | B2 * | 10/2013 | Alstad | F04B 43/1261 |
| | | | | 417/477.11 |
| 2005/0019186 | A1 * | 1/2005 | Davis | F04B 43/086 |
| | | | | 417/477.1 |
| 2005/0238515 | A1 | 10/2005 | Kent | |
| 2008/0243054 | A1 | 10/2008 | Mollstam et al. | |
| 2010/0129248 | A1 | 5/2010 | Mou | |
| 2010/0260633 | A1 * | 10/2010 | Ogawa | F04B 43/086 |
| | | | | 417/477.1 |
| 2011/0158823 | A1 * | 6/2011 | Wang | F04B 43/082 |
| | | | | 251/356 |
| 2013/0008843 | A1 * | 1/2013 | Choi | A61M 1/16 |
| | | | | 210/257.2 |
| 2015/0292529 | A1 * | 10/2015 | Thiebaud | F04B 43/12 |
| | | | | 92/2 |
| 2016/0017880 | A1 | 1/2016 | Maguire | |
| 2017/0106660 | A1 * | 4/2017 | Mizusaki | F04B 43/086 |
| 2018/0344914 | A1 * | 12/2018 | Von Gutfeld | A61M 1/1633 |

FOREIGN PATENT DOCUMENTS

| | | | | |
|---|---|---|---|---|
| FR | 2388255 A1 | 11/1978 | | |
| FR | 2388255 A * | 12/1978 | .......... | F04B 43/1284 |

OTHER PUBLICATIONS

European Patent Office, Written Opinion in International Patent Application No. PCT/GB2018/051310, 6 pp. (dated Jul. 7, 2018).
United Kingdom Intellectual Property Office, Search Report in United Kingdom Patent Application No. GB1707961.7, 1 p. (dated Oct. 26, 2017).

\* cited by examiner

PERISTALTIC PUMP

CROSS-REFERENCE TO RELATED APPLICATIONS

This application is a national phase application of International Patent Application No. PCT/GB2018/051310, filed May 15, 2018, which claims priority to United Kingdom Patent Application No. GB1707961.7, filed May 18, 2017, both of which are incorporated by reference herein in their entireties for all purposes.

The present invention relates to a peristaltic pump, with a single motor and a single rotor, which can be switched to act on alternative tracks to provide two modes of operation.

Peristaltic pumps are commonly used in medical procedures such as endoscopies, in which there is a need to supply liquid to a medical instrument for flushing and irrigation. These procedures also use pumps to provide suction to remove excess fluid. Conventionally two pumps are provided, one for supplying liquid under pressure and another for providing suction. The peristaltic pumps and other equipment are usually mounted on a moveable workstation, such as a wheeled trolley or IV Pole. Space is always at a premium on such workstations and it is desirable to make the footprint of the pump as small as possible and to reduce its weight. It is also known to employ a dual pump which includes two peristaltic pumps combined in one unit to reduce the footprint. However, such a unit is still relatively large and expensive due to the requirement for two motors, two pump heads and two tube management systems.

The present invention provides a peristaltic pump comprising a rotor rotatable by a motor, a plurality of rollers rotatably mounted on the rotor and first and second tracks mounted on opposite sides of the rotor, wherein each track is moveable between a first position adjacent to the rotor and a second position spaced from the rotor, wherein a flexible tube can be received between each track and the rotor.

Such a pump is capable of simple switching between one position in which the pump acts on a first tube received between the first track and the rotor and a second position in which the pump acts on a second tube received between the second track and the rotor. This reduces the footprint, weight and cost of the pump because it only requires a single motor and a single rotor.

Preferably, at least one stop member is provided to limit movement of the first and second tracks between their first and second positions.

Preferably, the first and second tracks are linked and moveable together such that as the first track moves towards the rotor, the second track moves away from the rotor and vice versa.

The first and second tracks may be linked by at least one connecting member slidably received in a block mounted in a fixed position relative to the rotor.

The pump may further comprise at least one latch to selectively retain the first and second tracks in their first and second positions.

The tracks may be configured for manual movement between the first and second position, or for automated movement.

The present invention also provides a fluid management system for use in a medical procedure comprising a peristaltic pump of the type described above, a first flexible tube mounted between the first track and the rotor, the second flexible tube mounted between the second track and the rotor, wherein the first tube is configured to supply liquid from a liquid reservoir to a channel in a medical instrument and the second tube is configured to apply suction to a channel in a medical instrument.

Conveniently, the first and second tubes may have portions which are joined together, separated by non-joined portions, wherein the tubes may be mounted on the pump with the non-joined portions fitted between the rotor and the first and second tracks respectively and joined portions located on either side of the rotor.

The invention will now be described in detail, by way of example only, with reference to the accompanying drawings in which.

Figure 1:
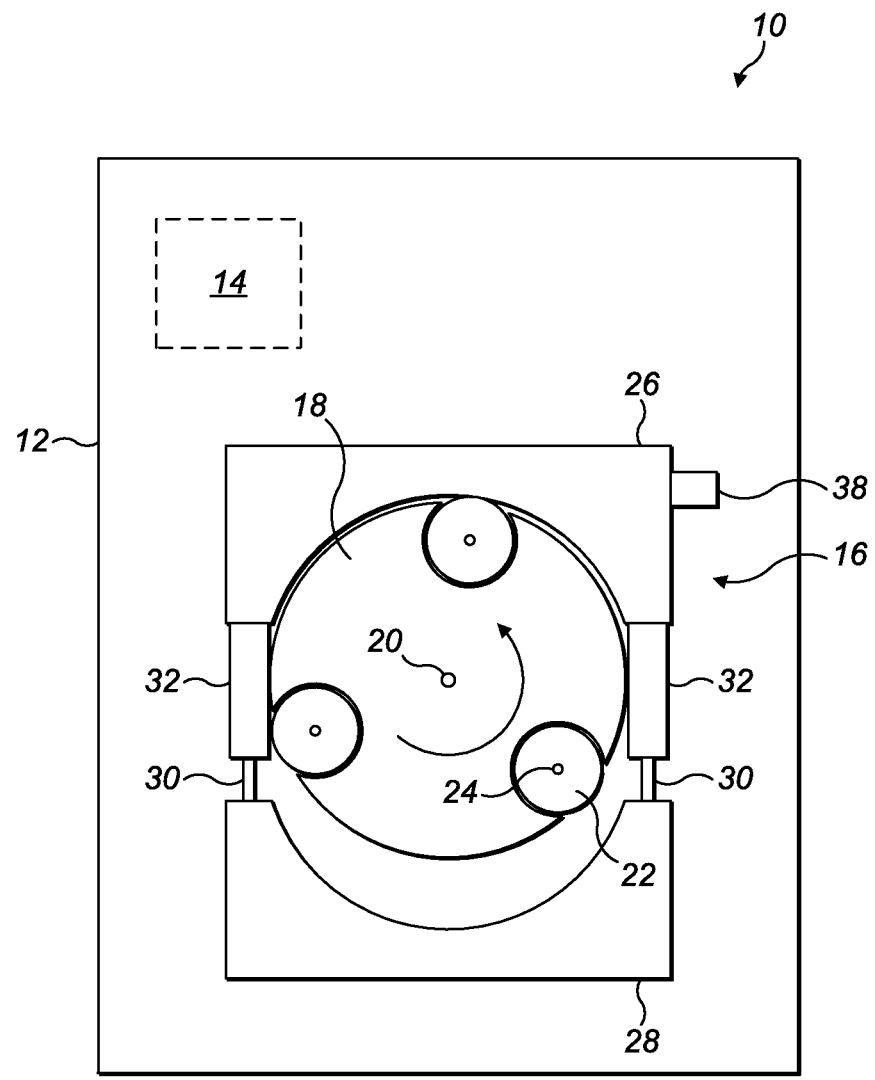
FIG. 1 illustrates schematically part of a peristaltic pump in accordance with the present invention, in its first position.

As shown in FIG. 1, a pump 10 in accordance with the present invention comprises a casing 12 containing a motor 14 in a conventional manner. A pump head 16 is mounted on the exterior of the casing 12. The pump head 16 comprises a rotor 18 mounted on the casing 12 and driven to rotate by the motor 14 about an axis 20. In this example, the rotor 18 is driven to rotate anti-clockwise.

In the normal way, the rotor 18 carries three rollers 22 each independently rotatable about its own central axis 24. Each roller 22 can be protruding, flush or sub-flush of the outer circumference of the rotor 18. In this example, the roller 22 protrudes slightly outside the rotor 18.

First and second tracks 26, 28 are mounted on opposite sides of the rotor 18. In this example a first track 26 is mounted above the rotor 18 and the second track 28 below the rotor 18. Each track 26, 28 comprises a body with an arcuate surface facing the rotor 18. Each track 26, 28 is moveable towards and away from the rotor 18. While the tracks 26, 28 could be moved independently, preferably the tracks 26, 28 are connected so that they move together. As the first track 26 moves towards the rotor 18, the second track 28 will move away from the rotor 18, and vice versa. In this example, the first and second tracks 26, 28 are joined by two connecting rods 30 which are slidably received in blocks 32 fixed to the casing 12 on either side of the rotor 18. The ends of the blocks 32 facing each track 26, 28 act as stop members to limit the up and down movement of the tracks 26, 28. It will be appreciated that the exact configuration of a stop member may be varied.

FIG. 1 shows the first track 26 in a first position, lowered until it is closely adjacent to the rotor 18, while the second track 28 is lowered into the second position in which it is spaced from the rotor 18.

Figure 2:
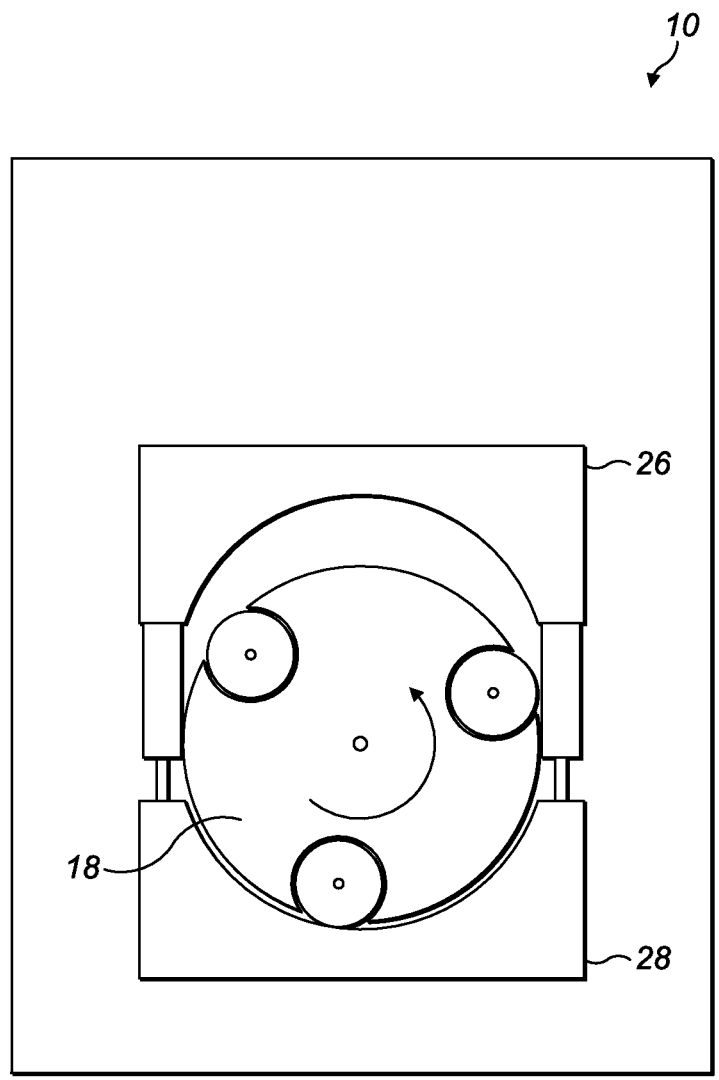
FIG. 2 illustrates the pump of FIG. 1, in a second position, with some parts omitted for clarity.

The tracks 26, 28 can be moved upwardly into the second position shown in FIG. 2, in which the first track 26 is spaced from the rotor 18 and the second track 28 closely adjacent to the rotor 18.

Figure 3:
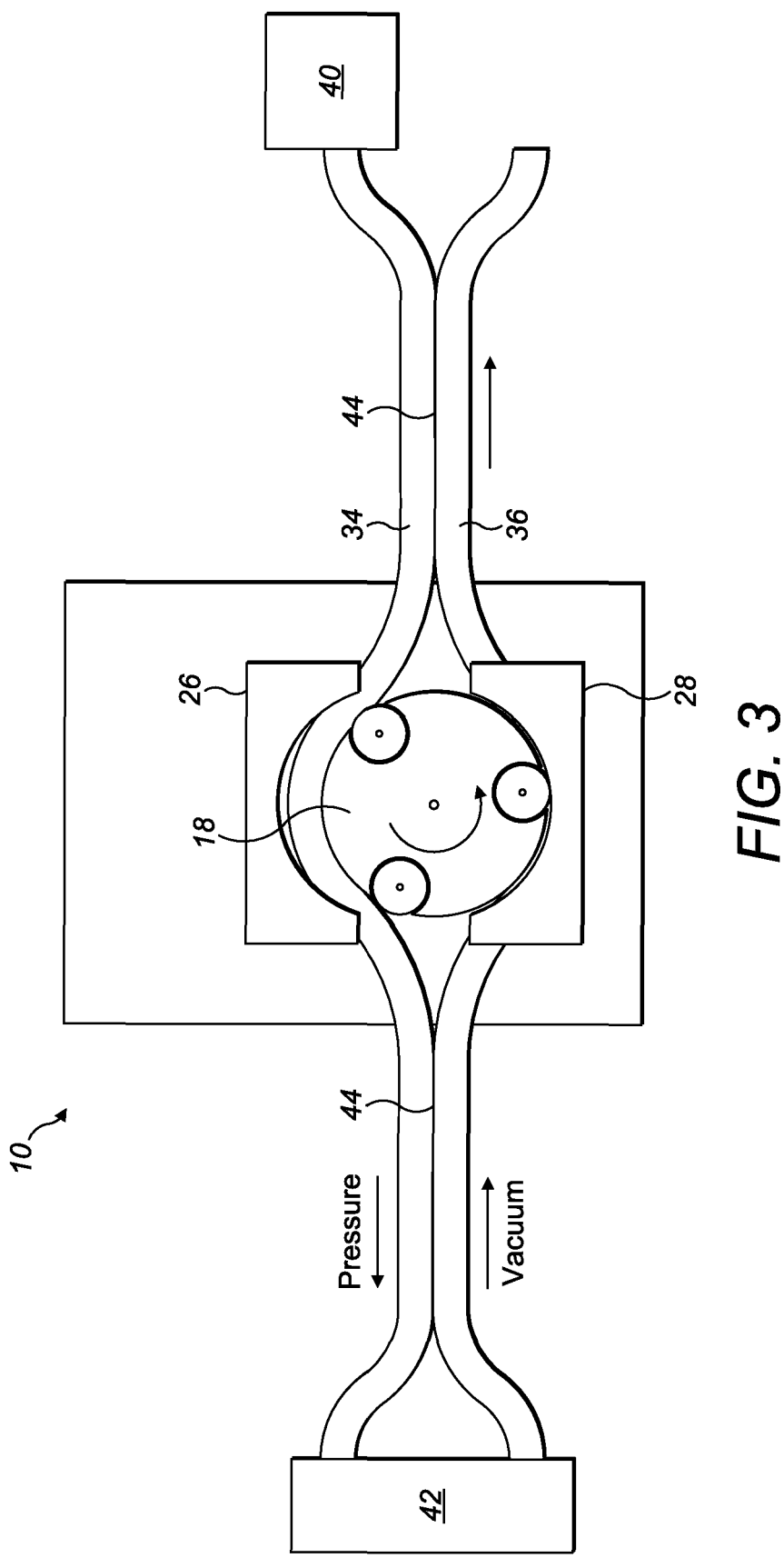
FIG. 3 illustrates the pump of FIG. 2, with flexible tubes in position, also with some parts omitted for clarity.

In use, flexible plastic tubes 34, 36 can be fitted between each the arcuate surfaces of track 26, 28 and the rotor 18 as shown in FIG. 3. Depending on the position of the tracks 26, 28 the rotor 18 will act either on one tube or the other.

In this example, the uppermost tube 34 fitted between the first track 26 and the rotor 18 is used to supply liquid to a medical instrument. Accordingly, upstream of the pump (on the right hand side in FIG. 3), the tube 34 is connected to a liquid reservoir 40 such as a standard plastic saline bottle. Downstream of the pump (on the left hand side in the Figure), the tube 34 is connected to a medical instrument 42. The lower tube 36 fitted between the second track 28 and the rotor 18 is used to apply suction. Therefore, its upstream end (on the left hand side in the Figure) is connected to the medical instrument and its downstream end (on the right hand side in the Figure) may vent to a collection receptacle.

When it is desired to apply suction, tracks 26, 28 are moved upwardly into the position shown in FIG. 3. The upper track 26 is spaced from the rotor 18 and therefore the rollers 22 do not act on the tube 34 as the rotor 18 rotates. The lower track 28 is closely adjacent to the rotor 18, compressing the tube 36 such that the rollers 22 act on the tube 36 as the rotor 18 rotates, creating suction in the tube 36.

When it is desired to supply pressurised liquid instead of suction, the tracks 26, 28 are simply shifted into the other position shown in FIG. 1 in which the upper tube 34 is now compressed between the upper track 26 and the rotor 18 and will be acted upon by the rollers 22, while the lower track 28 is spaced from the rotor 18 and the rollers 22 do not act on the lower tube 36.

Thus, a single rotor 18 rotatable by a single motor 14 only in one direction can be switched to operate on different tracks, in order to provide two different modes of operation.

The tracks 26, 28 may be provided with a latch device 38 to secure the tracks 26, 28 in position and avoid slipping or accidental changes of position. Such a latch 38 (illustrated only schematically in FIG. 1) may for example comprise a spring-biased projection on one or both tracks 26, 28 engageable in a recess in the pump casing 12 when the respective track 26, 28 in its first or second positions. Such a latch will provide a positive indication of when the tracks 26, 28 are properly positioned and a greater force must be applied to release the latch in order to move the tracks 26, 28 to avoid accidental movement. It will be appreciated that the exact configuration of the latch may be varied.

It is also possible for the tracks 26, 28 to be fixed and the rotor 18 to be moveable up and down relative to the tracks 26, 28. However, this is a more complex arrangement, given the need to connect the rotor 18 to the motor 14.

The tubes 34, 36 may be completely separate from each other, or for ease of handling, they may have portions 44 which are moulded or bonded together. As shown in FIG. 3, joined portions 44 may be provided on either side of a non-joined portion. The portions of the tubes 34, 36 which are not joined together can be separated and fitted around the rotor 18. This keeps the arrangement compact and makes it easier to handle the tubing.

Movement of the tracks 26, 28 relative to the rotor 18 between the two positions may be manual, with a user releasing the latch 38, if present, and simply moving the tracks 26, 28 up or down by hand. The system may also be automated, with a user selecting the required mode on a controller and movement of the tracks 26, 28 being actuated, for example by solenoids.

Thus, the present invention provides a peristaltic pump which is simply switchable to operate on two different tracks to provide two modes of operation, whilst using a single rotor and a single motor. This saves on space, weight and cost. The two modes of operation are preferably mutually exclusive so that the pump can run at its optimum efficiency one the selected mode of operation, without hindrance from the unselected mode.

The invention claimed is:

1. A peristaltic pump comprising a rotor rotatable by a motor, a plurality of rollers rotatably mounted on the rotor and first and second tracks mounted on opposite sides of the rotor, wherein each track is moveable between a first position adjacent the rotor and a second position spaced from the rotor, and the first and second tracks are linked by at least one connecting member slidably received in a block mounted in a fixed position relative to the rotor, the at least one connecting member maintaining the first and second tracks in a fixed position relative to one another whereby the first and second tracks are moveable together relative to the rotor such that as the first track moves towards the rotor, the second track moves away from the rotor and vice versa.

2. A peristaltic pump as claimed in claim 1, further comprising at least one stop member to limit movement of the tracks between the first and second positions.

3. A peristaltic pump as claimed in claim 1, further comprising at least one latch to selectively retain the tracks in their first and second positions.

4. A peristaltic pump as claimed in claim 1, wherein the tracks are configured for manual movement between the first and second positions.

5. A peristaltic pump as claimed in claim 1 wherein the tracks are configured for automated movement between the first and second positions.

6. A fluid management system for use in a medical procedure comprising a peristaltic pump as claimed in any preceding claim, a first flexible tube mounted between the first track and the rotor and a second flexible tube mounted between the second track and the rotor, wherein the first tube is configured to supply liquid from a liquid reservoir to a channel in a medical instrument and the second tube is configured to apply suction to a channel in a medical instrument.

7. A fluid management system as claimed in claim 6, wherein the first and second tubes have portions which are joined together, separated by a non-joined portion, wherein the tubes are mounted on the pump with the non-joined portion fitted between the rotor and the first and second tracks respectively and at least one of said portions that are joined together being located on either side of the rotor.

* * * * *